US009949758B2

(12) United States Patent
Vikinsky et al.

(10) Patent No.: US 9,949,758 B2
(45) Date of Patent: Apr. 24, 2018

(54) PRELOADED MEDICAL STRUTS (71) Applicant: Orthospin Ltd., Misgav (IL)

(72) Inventors: Ofer Vikinsky, Tzur-Yigal (IL); Jonatan Epstein, Ramat-HaSharon (IL); Ido Laufer, Herzlia (IL); Liraz Shlomoff, Rehovot (IL)

(73) Assignee: Orthospin Ltd., Misgav (IL)

( * ) Notice: Subject to any disclaimer, the term of this patent is extended or adjusted under 35 U.S.C. 154(b) by 0 days.

(21) Appl. No.: 15/125,254

(22) PCT Filed: Mar. 12, 2015

(86) PCT No.: PCT/IL2015/050268
§ 371 (c)(1),
(2) Date: Sep. 12, 2016

(87) PCT Pub. No.: WO2015/136544
PCT Pub. Date: Sep. 17, 2015

(65) Prior Publication Data
US 2017/0071632 A1    Mar. 16, 2017

Related U.S. Application Data

(60) Provisional application No. 61/951,560, filed on Mar. 12, 2014.

(51) Int. Cl.
*A61B 17/62* (2006.01)
*A61B 17/66* (2006.01)
(Continued)

(52) U.S. Cl.
CPC .......... *A61B 17/62* (2013.01); *A61B 17/6458* (2013.01); *A61B 17/66* (2013.01);
(Continued)

(58) Field of Classification Search
CPC ..... A61B 17/62; A61B 17/64; A61B 17/6458; A61B 17/66
See application file for complete search history.

(56) References Cited

U.S. PATENT DOCUMENTS 5,728,095 A    3/1998  Taylor
8,574,232 B1   11/2013 Ross et al.
(Continued)

FOREIGN PATENT DOCUMENTS

WO    WO 94/06364      3/1994
WO    WO 2015/136544   9/2015

OTHER PUBLICATIONS

International Search Report and the Written Opinion dated Jun. 29, 2015 From the International Searching Authority Re. Application No. PCT/IL2015/050268.
(Continued)

*Primary Examiner* — Julianna N Harvey (57) ABSTRACT

A medical device, comprising: a medical strut; a preloader configured to store energy, wherein the medical strut is configured to transform the energy stored in the preloader to a first force applicable to a bodily tissue; an actuator configured to apply a second force to adjust the length of the medical strut, thereby facilitating the transforming the stored energy to the first force; and a controller configured to control the actuator.

29 Claims, 6 Drawing Sheets

(51) Int. Cl.
*A61B 17/64* (2006.01)
*A61B 90/00* (2016.01)
*A61B 17/00* (2006.01)

(52) U.S. Cl.
CPC .... *A61B 90/06* (2016.02); *A61B 2017/00017* (2013.01); *A61B 2090/061* (2016.02); *A61B 2090/067* (2016.02)

(56) References Cited

U.S. PATENT DOCUMENTS

| | | |
|---|---|---|
| 2002/0010465 A1 | 1/2002 | Koo et al. |
| 2007/0225704 A1* | 9/2007 | Ziran ............... A61B 17/66 606/57 |
| 2007/0276378 A1* | 11/2007 | Harrison ............ A61B 17/0483 606/309 |
| 2008/0051779 A1 | 2/2008 | MacKenzie et al. |
| 2008/0234554 A1 | 9/2008 | Vvedensky et al. |
| 2008/0269741 A1 | 10/2008 | Karidis |
| 2010/0114103 A1 | 5/2010 | Harrison et al. |
| 2011/0196435 A1 | 8/2011 | Forsell |

OTHER PUBLICATIONS

International Preliminary Repoort on Patentability dated Sep. 22, 2016 From the International Bureau of WIPO Re. Application No. PCT/IL2015/050268.
Supplementary European Search Report and the European Search Opinion dated Dec. 1, 2017 From the European Patent Office Re. Application No. 15761768.9. (12 Pages).

* cited by examiner

PRELOADED MEDICAL STRUTS

RELATED APPLICATIONS

This application is a National Phase of PCT Patent Application No. PCT/IL2015/050268 having International filing date of Mar. 12, 2015, which claims the benefit of priority under 35 USC § 119(e) of U.S. Provisional Patent Application No. 61/951,560 filed on Mar. 12, 2014. The contents of the above applications are all incorporated by reference as if fully set forth herein in their entirety.

FIELD OF THE INVENTION

The invention relates to the field of medical devices.

BACKGROUND

External fixation devices are commonly used to fixate, manipulate, distract, or apply force to one or more bone segments for the treatment of various skeletal defects, such as fracture repair, joint fixation, limb lengthening and deformity correction. External fixation devices may include fixators such as plates and multi-planar or mono-lateral/mono rails. Multi-planar external fixators may comprise one or more rings or ring sections attached to pins and/or wires that secure fixation of the bone. A mono-lateral or mono-rail fixator may be attached to pins, wires, or rods. The fixators may interconnect with one or more adjustable struts, to fixate the fracture or the joint, and enabling mono lateral or three dimensional movement of the bone segments.

The length of the struts is typically adjusted manually by the patient several times daily in a process that is often painful, difficult and complicated. Lack of compliance, or erroneous adjustment of the struts can cause severe complications, and is a common contraindication for such procedures. Additionally, effective treatment typically requires the exertion of a large force, which may be difficult and expensive to operate by a medical strut.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

There is provided, in accordance with an embodiment, a medical device, comprising: a medical strut; a preloader configured to store energy, wherein the medical strut is configured to transform the energy stored in the preloader to a first force applicable to a bodily tissue; an actuator configured to apply a second force to adjust the length of the medical strut, thereby facilitating the transforming the stored energy to the first force; and a controller configured to control the actuator.

In some embodiments, the actuator comprises a motor, and wherein the second force comprises a torque.

In some embodiments, the adjusting of the length of the medical strut comprises lengthening the medical strut.

In some embodiments, the first force is exerted longitudinally along the lengthwise axis of the medical strut.

In some embodiments, the medical strut is connected to one or more external fixation devices that are connected to the bodily tissue via one or more pins, thereby transferring the first force to the bodily tissue.

In some embodiments, the medical strut connects to the one or more external fixation devices via a mechanism that provides polyaxial movement of the medical strut with respect to the one or more orthopedic fixation devices.

In some embodiments, the actuator is further configured to shorten the medical strut independently of the preloader.

In some embodiments, there is further provided a threaded shaft that is configured to rotate with the actuator, wherein the actuator is connected to a one-way bearing, thereby allowing the shortening of the medical strut independently of the preloader.

In some embodiments, the preloader comprises a spring.

In some embodiments, the spring comprises a sealed cavity that is configured to store a fluid under high pressure.

In some embodiments, there is further provided a piston that seals the cavity, wherein the second force applied by the actuator is configured to cause the piston to withdraw from the cavity, thereby lengthening the medical strut.

In some embodiments, the spring comprises a mechanical spring.

In some embodiments, the controller controls any of: a duration for operating the actuator, a force exerted by the actuator, or a target medical strut length.

In some embodiments, the controller controls a target bone lengthening rate.

In some embodiments, the controller is configured to receive an indicator from a sensor and apply the indicator to monitor, control and/or synchronize the operation of the medical strut.

In some embodiments, the controller is configured to send the indicator to an external controlling device.

In some embodiments, the controller is configured to receive a parameter for controlling any of the components of the medical device from the external controlling device in response to the external controlling device receiving the indicator.

There is provided, in accordance with an embodiment, a kit for providing a medical treatment, comprising: a medical strut comprising a preloader configured to store energy, wherein the medical strut is configured to transform the energy stored in the preloader to a first force applicable to a bodily tissue, an actuator configured to apply a second force to adjust the length of the medical strut, thereby facilitating the transformation of the stored energy to the first force, and a controller that is configured to control the actuator; and an external fixation device configured to connect to the medical strut and to connect to the bodily tissue via one or more pins, thereby transferring the first force to the bodily tissue.

In some embodiments, the actuator comprises a motor, and wherein the second force comprises a torque.

In some embodiments, the adjusting of the length of the medical strut comprises lengthening the medical strut.

In some embodiments, the first force is exerted longitudinally along the lengthwise axis of the medical strut.

In some embodiments, the medical strut connects to the one or more external fixation devices via a mechanism that provides polyaxial movement of the medical strut with respect to the one or more orthopedic fixation devices.

In some embodiments, the actuator is further configured to shorten the medical strut independently of the preloader.

In some embodiments, there is further provided a threaded shaft that is configured to rotate with the actuator, wherein the actuator is connected to a one-way bearing, thereby allowing the shortening of the medical strut independently of the preloader.

In some embodiments, the preloader comprises a spring.

In some embodiments, the spring comprises a sealed cavity that is configured to store a fluid under high pressure.

In some embodiments, there is further provided a piston that seals the cavity, wherein the second force applied by the actuator is configured to cause the piston to withdraw from the cavity, thereby lengthening the medical strut.

In some embodiments, the spring comprises a mechanical spring.

In some embodiments, the controller controls any of: a duration for operating the actuator, a force exerted by the actuator, or a target medical strut length.

In some embodiments, the controller controls a target bone lengthening rate.

In some embodiments, the controller is configured to receive an indicator from a sensor and apply the indicator to monitor, control and/or synchronize the operation of the medical strut.

In some embodiments, the controller is configured to send the indicator to an external controlling device.

In some embodiments, the controller is configured to receive a parameter for controlling any of the components of the kit from the external controlling device in response to the external controlling device receiving the indicator.

There is provided, in accordance with an embodiment, a medical device, comprising: a medical strut; a hydraulic mechanism configured to apply a force to adjust the length of the medical strut, wherein the medical strut is configured to transfer the exerted force to a bodily tissue; and a controller that is configured to control the medical strut and/or the hydraulic mechanism.

In some embodiments, the medical strut connects to one or more external fixation devices that are connected to the bodily tissue via one or more pins, thereby transferring the force to the bodily tissue.

In some embodiments, the one or more external fixation devices is configured to store a fluid, and wherein the hydraulic mechanism is configured to pump the stored fluid for applying the force.

In some embodiments, the controller controls any of: a duration for operating the actuator, a force exerted by the actuator, or a target medical strut length.

In some embodiments, the controller controls a target bone lengthening rate.

In some embodiments, the controller is configured to receive an indicator from a sensor and apply the indicator to monitor, control and/or synchronize the operation of the medical strut.

In some embodiments, the controller is configured to send the indicator to an external controlling device.

In some embodiments, the controller is configured to receive a parameter for controlling any of the components of the medical device from the external controlling device in response to the external controlling device receiving the indicator.

There is provided, in accordance with an embodiment, a method comprising: transforming, via a medical strut, energy stored by a preloader to a first force for applying to a bodily tissue; applying, via an actuator, a second force to adjust the length of the medical strut, thereby facilitating the transformation of the stored energy to the first force; and controlling the actuator.

In some embodiments, the actuator comprises a motor, and wherein the second force comprises a torque.

In some embodiments, the adjusting of the length of the medical strut comprises lengthening the medical strut.

In some embodiments, the method further comprises exerting the first force longitudinally along the lengthwise axis of the medical strut.

In some embodiments, the method further comprises connecting the medical strut to one or more external fixation devices that are connected to the bodily tissue via one or more pins, thereby transferring the first force to the bodily tissue.

In some embodiments, the method further comprises providing polyaxial movement of the medical strut with respect to the one or more orthopedic fixation devices.

In some embodiments, the method further comprises shortening the medical strut independently of the preloader.

In some embodiments, shortening the medical strut independently of the preloader further comprises causing a threaded shaft to rotate with the actuator, wherein the actuator is connected to a one-way bearing.

In some embodiments, the method further the preloader comprises a spring.

In some embodiments, the spring comprises a sealed cavity that is configured to store a fluid under high pressure.

In some embodiments, the method further comprises sealing the cavity with a piston, wherein the second force applied by the actuator is configured to cause the piston to withdraw from the cavity, thereby lengthening the medical strut.

In some embodiments, the spring comprises a mechanical spring.

In some embodiments, the method further comprises controlling any of: a duration for operating the actuator, a force exerted by the actuator, or a target medical strut length.

In some embodiments, the method further comprises controlling a target bone lengthening rate.

In some embodiments, the method further comprises receiving an indicator from a sensor and applying the indicator to monitor, control and/or synchronize the operation of the medical strut.

In some embodiments, the method further comprises sending the indicator to an external controlling device.

In some embodiments, the method further comprises receiving a parameter for controlling any of the components of the medical device from the external controlling device in response to the external controlling device receiving the indicator.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

DETAILED DESCRIPTION

Disclosed herein is an orthopedic strut that is configured for connecting to one or more external fixation devices, such as rings or a monorail, that may, in turn, be connected to a bodily tissue of a patient, such as a bone, ligament, or joint, via one or more connecting pins, wires, nails or plates, for therapeutic purposes. The strut may have an adaptable length, and may store a quantity of energy such as mechanical, electrical, chemical, magnetic, or other, that may be released in a controlled manner to exert a lengthwise force to adjust the length of the strut. This lengthwise force may be transferred to the connected fixation device and applied to the connected bodily tissue.

Figure 1A:
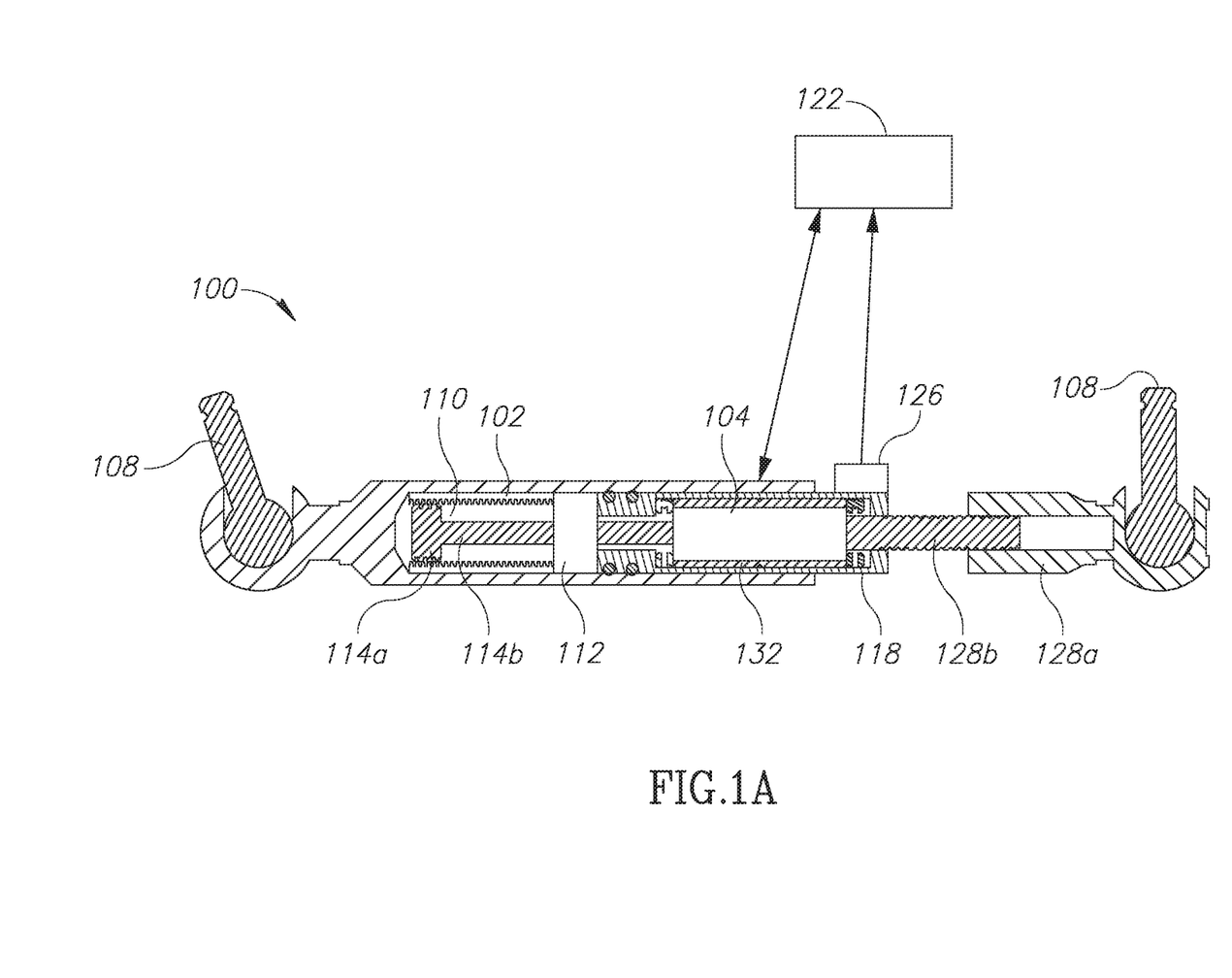
FIGS. 1A-D illustrate perspective and cross-sectional views of a strut, in accordance with an embodiment.
Figure 1B:
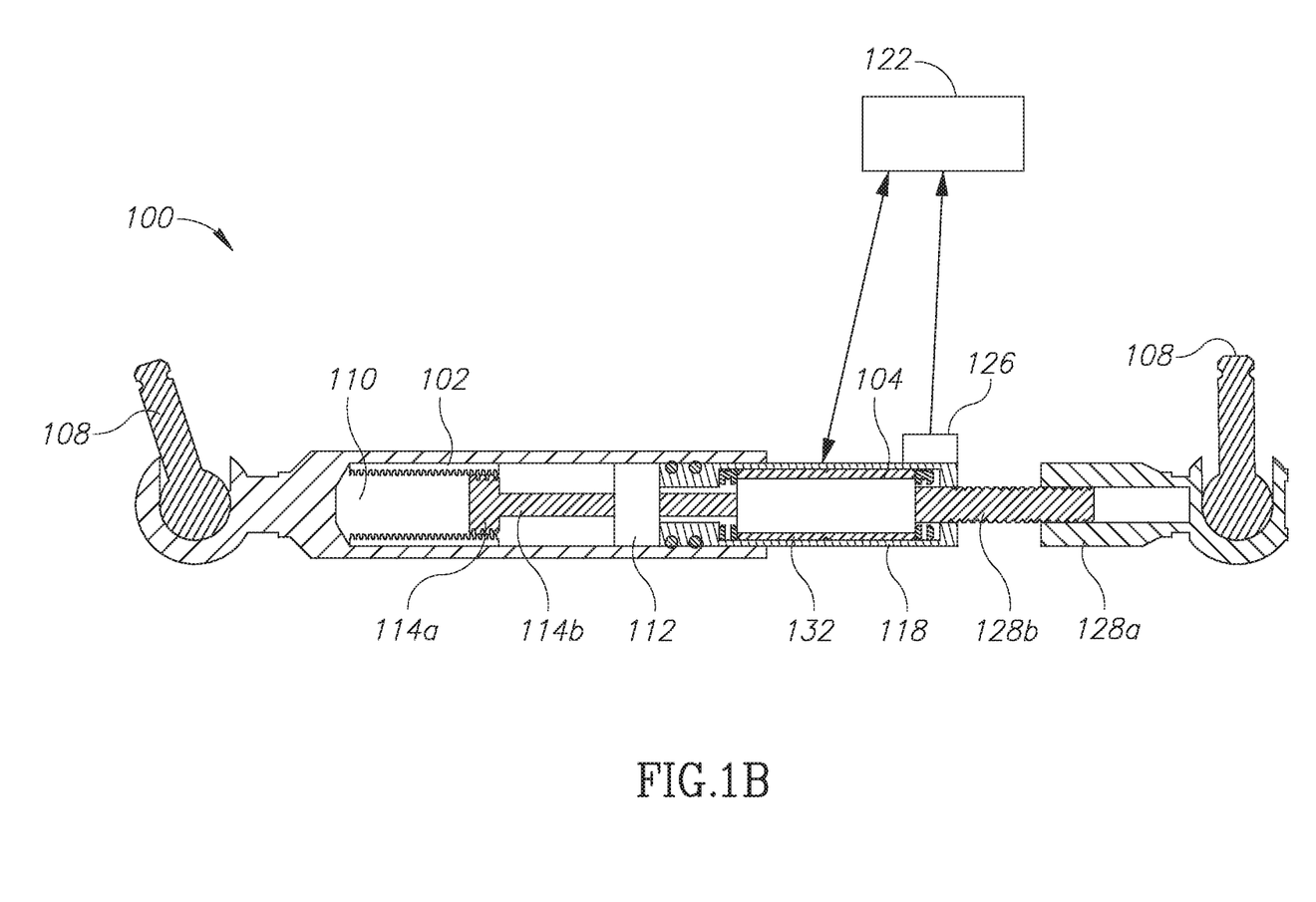

Reference is made to FIGS. 1A-B which, taken together, show a cross-sectional view of a strut 100 in compressed and expanded states, respectively, in accordance with an embodiment. A preloader 102 may be provided with strut 100 for storing energy, such as pressure. Strut 100 may transform the energy stored by preloader 102 to a force for applying to a bodily tissue. The force may be exerted longitudinally along the lengthwise axis of the strut. An actuator 104 provided with strut 100 may apply a secondary force for adjusting the length strut 100, such as by lengthening strut 100 as shown in FIG. 1A. In one embodiment, preloader 102 is provided within, and integral to strut 100.

Actuator 104 may comprise an electrical, magnetic, mechanical or other means for producing a force to release energy stored in preloader 102. For example, actuator 104 may comprise a motor, a magnetic, chemical, or mechanical element such as a torsion spring or torsions bar. The substantially large force provided by strut 100 for therapeutic treatment may be supplied via preloader 102, whereas actuator 104 may merely be required to provide a secondary force that is sufficient to controllably release the energy stored in preloader 102. Thus, actuator 104 may apply a relatively small secondary force, or torque compared to the primary force exerted by preloader 102. In one embodiment, actuator 104 is provided within, and integral to strut 100.

For example, preloader 102 may provide a force of 1500 Newtons (N) that may be exerted on the bodily tissue via strut 100, whereas actuator may provide a torque ranging from as little as 0.05 Newtons*meter (N*m) to 0.5 N*m.

In one embodiment, actuator 104 may comprise a motor that may be powered by any suitable power supply, such as a battery. Actuator 104 may generate linear and/or rotational motion, and may comprise any suitable type of motor, such as a brush motor, brushless motor, direct current/alternating current (DC/AC) servo or Steeper motor, an may include any suitable elements, such as a Piezo linear actuator, electromagnet, chemical reaction, pump, or hydraulic pump, to name a few. In an embodiment, the diameter of actuator 104 may range from 6-20 millimeters (mm), and have an operating voltage ranging from 6-24 volts (V), with a holding torque ranging from 15-30 grams/centimeter (gr/cm). In one embodiment, the operating voltage may be at 12V. Optionally, actuator 104 have an operating Electric Power ranging from 0.03-0.350 Watt (W), with a torque ranging from 0.05-0.5 Newton-Meter-50.

Figure 1C:
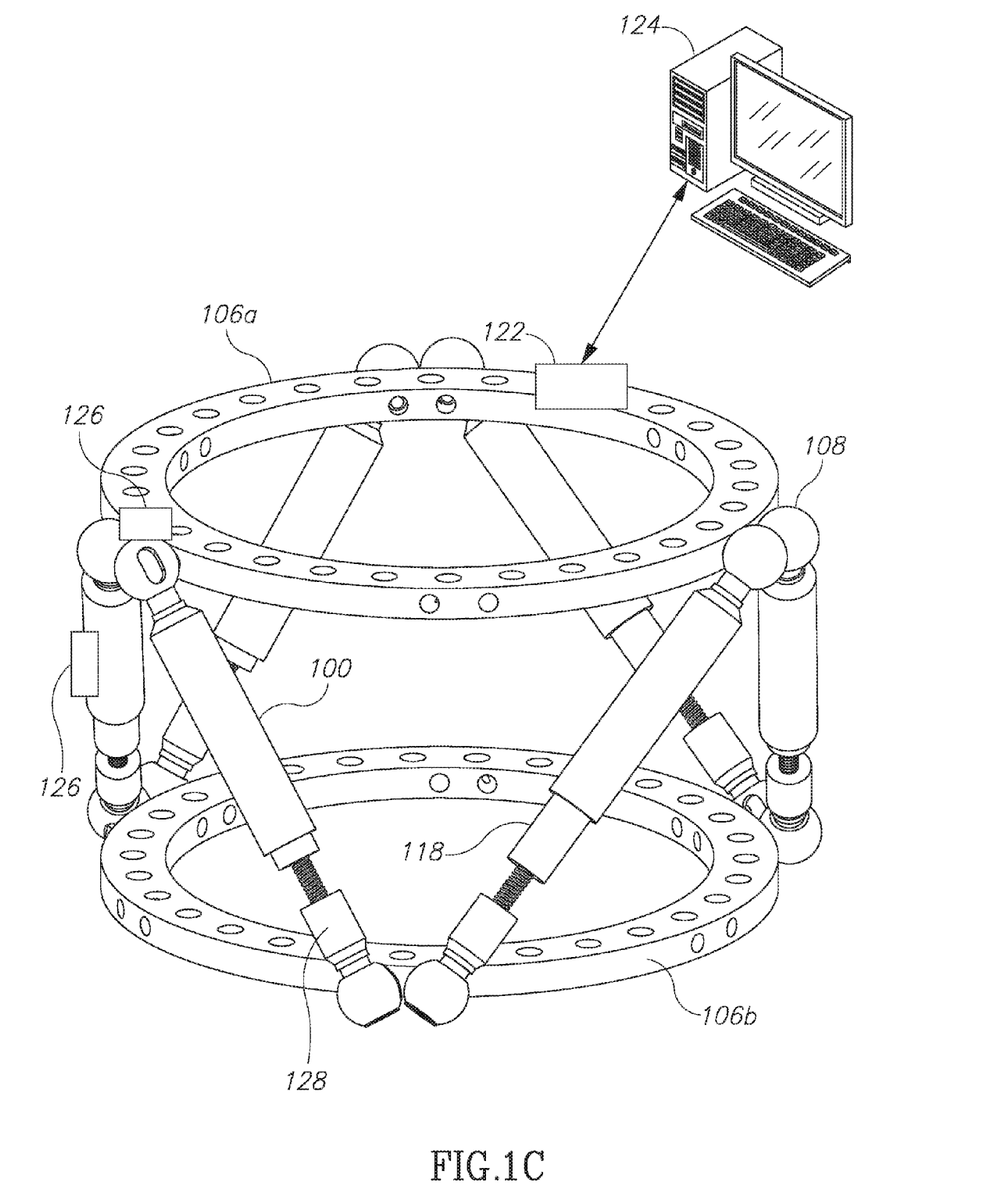
Figure 1D:
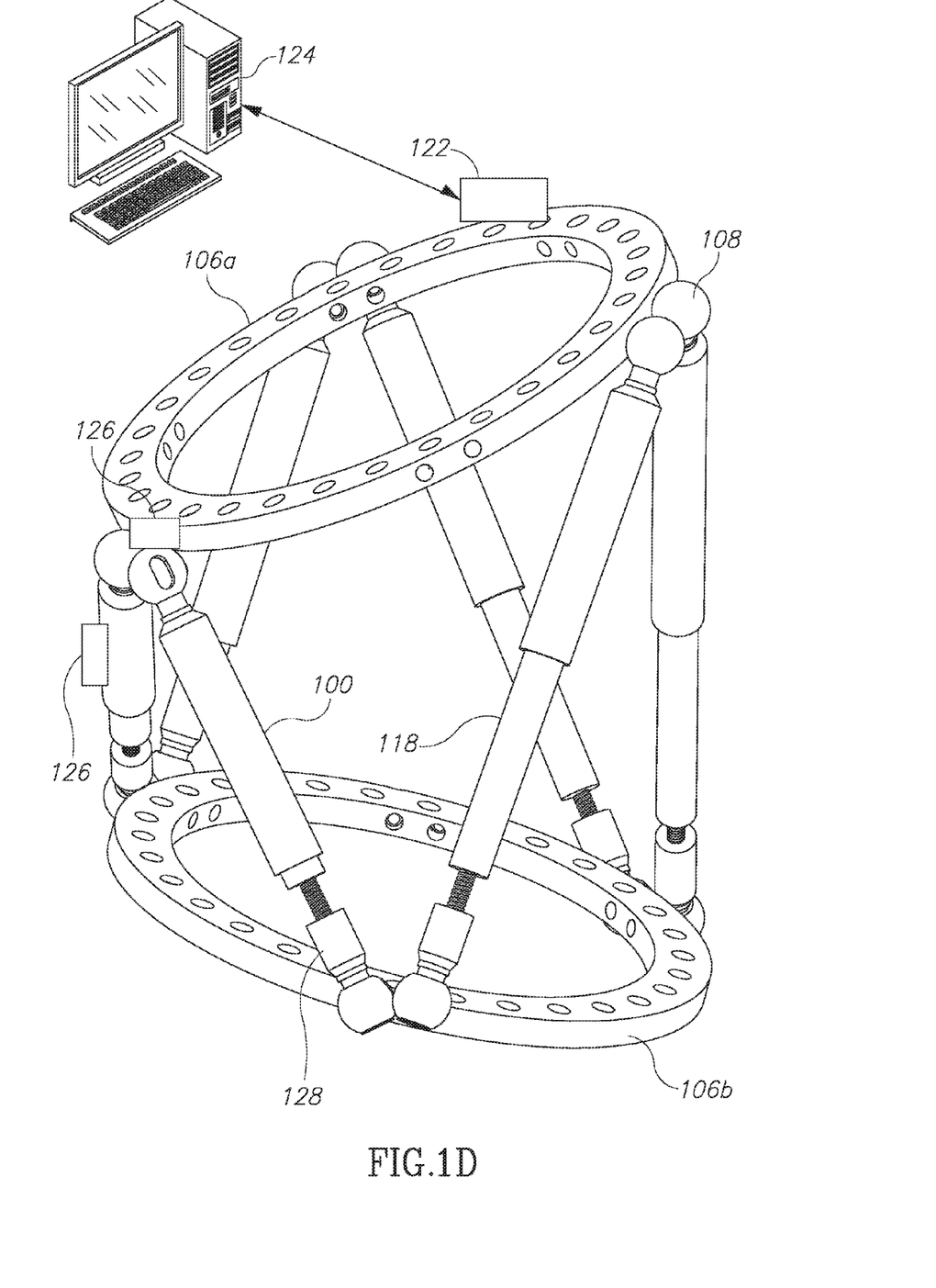

Reference is now made to FIGS. 1C-D, which taken together, illustrate multiple struts 100 in shortened and lengthened states, respectively, connected to one or more external fixation devices, in accordance with an embodiment. For the purpose of clarity only, several features of FIGS. 1C-D are not labeled, for example, only one strut out of six struts shown, is labeled. However it is to be understood that any features described and/or labeled in FIGS. 1A-B similarly apply to FIGS. 1C-D.

The ends of strut 100 may be connected to one or more external fixators, such as rings 106a and 106b, nails, screws, plates, or a monorail, that may be connected to the bodily tissue via one or more pins (not shown). Thus, the lengthening force exerted by strut 100 may be transferred to the bodily tissue via connected external fixators 106a and 106b and the pins.

In an embodiment, strut 100 may connect to the one or more external fixators, such as bone fixators 106a and 106b via a ball and pin joint 108. The strut 100 may be connected to fixators 106a and 106b as part of a surgical procedure in an operating room. Strut 100 may be provided compressed and ready for installing, alternatively, an operator may compress strut 100 using a compression tool or jig.

Strut 100 may attach to an external fixator via any suitable mechanism that provides polyaxial movement with respect to the fixator. In an embodiment, strut 100 may be provided with two ball and pin joints 108 each positioned at an opposite end of strut 100. Ball and pin joint 108 may allow each strut 100 to rotate in three dimensions relative to any of fixators 106a and 106b, allowing each strut 100 to lengthen independently of any other strut 100 while attached to fixators 106a and 106b. By providing multiple struts 100 connected to one or more fixators 106a and 106b via multiple ball and pin joints 108, multiple forces spanning multiple planes may be applied to the bodily tissue.

Ball and pin joint 108 may be comprised of any suitable material, such as stainless steel, aluminum, titanium or a combination thereof. In one embodiment, the length of the pin portion of ball and pin joint 108 may range from 10-20 mm. In one embodiment, the pin portion may be 16 mm in length. In one embodiment, the diameter of the pin portion may range from 4-6-mm. In one embodiment, the diameter of the pin portion is 5 mm. In one embodiment, the diameter of the ball portion of ball and pin joint 108 may range from 10-15 mm. In one embodiment, the diameter of the ball portion of ball and pin joint 108 is 12 mm.

Referring back to FIGS. 1A-B, preloader 102 may comprise a spring for storing and releasing the energy. In one embodiment, preloader 102 may comprise a sealed cavity 110 for storing a fluid, such as air, under high pressure. Cavity 110 may comprise a tube that is closed at one end, and that is sealed at the other end by a piston 112 and one or more sealing rings (not shown) made of rubber, or silicone, or any other suitable material. Piston 112 may move linearly within cavity 110 to compress and/or release fluid pressure within cavity 110.

In an embodiment, cavity 110 may be made of aluminum, carbon enforced polymers, or any other lightweight and strong material that is suitable to contain pressure of approximately 30-100 atmospheres (atm). In one embodiment, cavity 110 may have a diameter of between 10-30 mm. The length of cavity 110 may range from approximately 20 to 400 mm, and may be set in accordance with a strut lengthening requirement.

In an embodiment, piston 112 may be made of aluminum or stainless steel and may have a cap with a diameter of between 10-30 mm with sufficient tolerance to fit within cavity 110. The length of piston 112 may range from 50-100 mm and may vary to correspond to the overall length of strut 100.

The torque applied by motor 104 may cause piston 112 to withdraw from cavity 110 and lengthen strut 100 by a corresponding axial distance, as shown in FIG. 1A. The fluid pressure within cavity 110 may be sufficiently high such that the release of pressure resulting from the withdrawal of piston 112 may be negligible relative to the pressure prior to the release, thereby exerting relatively strong force on piston 112 following the withdrawal of piston 112 and resulting in the lengthening of strut 100. The high pressure maintained within cavity 110 throughout the lengthening of strut 100 may be applied on piston 112 following its withdrawal from cavity 100, and may be transferred to the bodily tissue.

In an embodiment, an internal lock may be provided (not shown) to prevent the release of pressure by strut 100 when actuator 104 is not operational.

In an embodiment, piston 112 may connect to a worm pinion 114a coupled with a shaft 114b that are provided to maintain the relatively high pressure within cavity 110. The relatively small torque generated by actuator 104 may be transferred via shaft 114b to worm pinion 114a, causing worm pinion 114a to rotate along a thread provided within cavity 110. When lengthening strut 100, a counterclockwise rotation by actuator 104 may cause pinion 114a to at least partially 'unscrew' from cavity 110, thereby causing piston 112, connected to pinion 114a and shaft 114b, to withdraw from cavity 100 accordingly, while maintaining the airtight seal for cavity 110.

In an embodiment, piston 112 may connect to shaft 114b in a manner that allows piston 112 to slip rotationally with respect to shaft 114b, such that the motion of piston 112 is substantially longitudinal along the length of strut 110.

In an embodiment, pinion 114a may be made of hardened stainless, and may comprise a steel worm gear with a diameter of 6-16 mm, and a length of 10-100 mm, with peach of 0.5-2 mm. Actuator 104 in combination with pinion 114a and shaft 114b may yields a controlled elongation of strut 100 in increments of 0.05-0.1 mm.

In one embodiment, a gear set 116 (not shown) may be provided to adjust the speed and torque of actuator 104 and translate a first angular rotation by actuator 104 to a second angular rotation by pinion 114a and shaft 114b. In an embodiment, gear set 116 may be configured to translate the first angular rotation to the second angular rotation in accordance with a desired shortening and/or lengthening of strut 100. Additionally or alternatively, gear set 116 may adjust a relatively fast rotation by actuator 104 producing a small torque, to a slower rotation producing a larger torque that is sufficient to overcome the friction between pinion 114a and shaft 114b and enable piston 112 to elongate strut 100.

Gear set 116 may be made of plastic and/or stainless steel or a combination thereof. In one embodiment, gear set 116 may have a reduction ratio of 1:100 to 1:1000, a diameter ranging between 6-16 mm, and a height ranging between 10-50 mm. Gear set 116 together with actuator 104 may provide torque ranging from 0.05-1.0 Newton-meters (NM) at the exit from the gear.

In one embodiment, actuator 104, and/or pinion 114a and shaft 114b and/or gear set 116 may be housed in a housing 118, such as comprising a tube, box or other hollow feature made of aluminum, plastic, stainless steel, or other suitable material.

A controller 122, comprising an electronic and/or software element, and/or mechanical, and/or other elements and any combination thereof, may be provided to control and/or coordinate the operation of any of the components within strut 100. Controller 122 may comprise a processor with a user interface (UI) to allow loading controller 122 with a treatment plan, such as a prescription, by a physician. Controller 122 may be loaded with a treatment program using any suitable wired and/or wireless means.

For example, a treatment plan may include a definition for a target bone lengthening within a set time period, and/or rate, and/or direction, and/or target force, and/or according to a schedule.

Controller 122 may include a computing application for computing one or more mechanical, electrical, or other signals for controlling any of the components of strut 100 to implement the treatment plan. For example, controller 122 may compute the number of turns of the motor or gear, or the force that must be exerted by actuator 104 to implement the target bone lengthening, or the target bone lengthening rate, or a target strut length, and may determine a corresponding schedule for the operation of actuator 100. Such a schedule may define a time of day, and duration measured in hours or minutes for operating actuator 104.

In one embodiment, controller 122 may simultaneously control multiple struts 100 that are connected to one or more external fixation devices attached to the patient. Controller 122 may synchronize the motion of any of the connected struts 100 according to the treatment plan, thereby controlling the position of struts 100 in relation to fixators 106a and 106b in multiple dimensions, and thus, control the relative position of the connected bodily tissue.

In another embodiment, a master controller (not shown) may control and/or synchronize each of multiple controllers 122 provided with multiple struts 100. Controller 122 and/or master controller may be positioned in any suitable manner that allows communication between controller 122 and the elements of strut 100 controlled by controller 122. For example, controller 122 may positioned within, affixed to, or adjacent to strut 100. Alternatively, controller 122 may be disposed with any external fixation device connected to strut 100.

Controller 122 may send one or more indicators regarding the operation of strut 100 to an external controlling device 124, such as a computer, cellular phone or tablet of a supervising physician, using wired or wireless means, such as Bluetooth, RF, Infra Red Wi-Fi or any other suitable communication technique that enables bi-directional communication between controller 122 and device 124. For example, controller 122 may send the physician regular indicators regarding the lengthening of strut 100, or the angular movement produced by actuator 104. The indicators may be sent according to a schedule, such as daily or weekly, allowing the physician to monitor the progress of the treatment on the patient.

One or more sensors 126 may be provided to measure the indicators corresponding to the operation strut 100. Controller 122 may receive the indicator from sensor 126, and apply it to monitor, control and/or synchronize the operation of strut 100. In one embodiment, multiple sensors 126 may be provided with a single strut 100 for measuring multiple indicators of that strut, such as bodily temperature, electro-optic measurements, distance and/or angular measurements of the position of the bodily tissue.

In one embodiment, controller 122 may receive from device 124 one or more parameters for controlling strut 100, such as a treatment program, or an adjustment to the preloaded treatment program in response to an indicator that was sent to and analyzed by device 124.

In another embodiment, a sensor 126 may be provided for measuring an indicator for multiple struts 100. Sensors 126 may be disposed at any suitable location, such as with strut 100 or with any of fixators 106a and 106b. Sensors 126 may determine an angular rotation, or a moment exerted by actuator 104 or any other rotating components of strut 100, such as worm pinion 114a. Alternatively, sensors 126 may measure the lengthening and/or shortening of strut 100, or the linear force and/or the stress applied by strut 100 to fixators 106a and 106b. The indicators measured by sensors 126 may be sent to controller 106 using any suitable wired or wireless means. Controller 122 may use the indicators received by any of sensors 126 to synchronize and coordinate the operation of multiple struts 100, such as in accordance with the embodiment of FIGS. 1C-D.

In one embodiment, sensor 126 may trigger an alert in case of malfunction or emergency. The alert may be sensed by the patient and/or the operator via device 124. A trigger may be provided to shut down the system, such as in case of an emergency.

Similarly, controller 122 may receive one or more instructions from device 124 such as adjustments to the operation of strut 100 in response to the updates. Controller 122 may compute the corresponding electrical and/or mechanical signals that are required to implement the desired adjustments and apply them accordingly.

In an embodiment, strut 100 may include a shortening mechanism for shortening strut 100 independently of preloader 102. The shortening mechanism may comprise a threaded casing 128a coupled to a shaft 128b, such as a screw, for adjusting the length of strut 100, and may operate independently of pinion 114a, shaft 114b, and piston 112. In one embodiment, the diameter of shaft 128b may range from M5-M8, and casing 128a may have a diameter of 20 mm, and a height of 10 mm, and may be made of any suitable material, such as plastic or aluminum.

In one embodiment, in addition to motor shaft 114b, actuator 104 may be affixed to shaft 128b in a manner that allows shaft 128b to rotate with actuator 104. Actuator 104 may be operable in both clockwise and counterclockwise directions to operate both the shortening mechanism, and pinion 114a, shaft 114b, and piston 112 for lengthening strut 100, respectively, in accordance with a controlling signal from controller 122.

For example, to lengthen strut 100, controller may send a 'lengthen' signal to actuator 104, which may cause actuator 104 to generate a torque in a counterclockwise direction. Actuator 104 may be connected to a one-way bearing 132 such as a ratchet mechanism, which may prevent any counterclockwise rotation of actuator 104, thereby transferring the counterclockwise torque generated by actuator 104 to shaft 114b for lengthening strut 100, as described above.

Conversely, to shorten strut 100, controller may send a 'shorten' signal to actuator 104 which may cause actuator 104 to generate a torque in a clockwise direction. The relatively high resistance to a clockwise rotation exerted by preloader 102 on shaft 114b may prevent shaft 114b from rotating, thereby transferring the clockwise torque onto actuator 104, which may be enabled to rotate clockwise by one-way bearing 132. The resulting clockwise rotation by actuator 104 may cause threaded shaft 128b to rotate accordingly, and 'screw' shaft 128b into housing 128a to shorten strut 100 accordingly.

Thus, by providing an actuator 104 with one-way bearing 132 and affixed threaded shaft 128b, actuator 104 may shorten strut 100 independently of preloader 102.

By precluding the compression of preloader 102 by actuator 104 when shortening strut 100, actuator 104 may comprise a relatively simple, low-power motor for both lengthening and shortening strut 100. Additionally, the force exerted on strut 100 by the bodily tissue connected to strut 100 via any of the external fixators described above many contribute to the shortening of strut 100 via the shortening mechanism.

In one embodiment, ratchet mechanism 132 may comprise a toothed wheel approximately 15 mm in diameter with 10-15 teeth or a toothed bar 30-40 mm long. Ratchet mechanism 132 may be comprise a latch made from stainless steel, or other hardened medical grade material for enabling and/or disabling the rotation of actuator 104.

In an embodiment, the spring may comprise a mechanical spring that may be housed within strut 100. The spring may comprise any suitable spring, such as a compression spring, or torsion bar, to name a few. In one embodiment, the spring may comprise a high carbon steel helical leaf spring with internal diameter of approximately 4-10 mm, and preferably 6 mm, an external diameter of approximately 15-25 mm, preferably 18 mm, and a height of approximately 20-40 mm preferably 30 mm, with a leaf width of approximately 0.1-1 mm, preferably 0.5 mm.

A loading port may be provided for loading the spring via any suitable loading method, such as by using a wrench or drill. In one embodiment, the spring loading port may have a triangular, square, hexagonal or torx element with a 4-8 mm diameter and 3-6 mm length, and which may connect to a wrench with a matching bit for the purpose of manually loading the spring.

The spring may be disposed within a shaft. In one embodiment, the shaft may comprise a stainless steel bar with a diameter ranging from approximately 4-8 mm and preferably 6 mm, and a length of up to approximately 100 mm. A first end of the shaft may connect to the loading port, and the second end of the shaft may be provided with a screw (not shown) that is adapted to fit with a bolt (not shown). The screw together with the bolt may couple with actuator 104 and cause the elongation and/or shortening of strut 100.

In an embodiment, a ratchet mechanism comprising a gear and a latch may be provided for loading preloader 102. In one embodiment, ratchet gear may comprise a toothed wheel with an approximate diameter ranging from 10-20 mm, and preferably 12 mm. The ratchet mechanism may be coupled with a shaft to allow a one-way rotation for loading preloader 102.

In another embodiment, an escapement mechanism may be provided to regulate the release of preloader 102 by motor 104. The escapement mechanism may comprise a stainless steel toothed wheel that engages with a stopper, or pendulum and may engage with motor via one or more hinges and/or gears, thereby regulating the release of preloader 102 by one tooth engagement, or 'click', at a time by rotating the screw and bolt mechanism that elongates strut 100. The stopper may comprise a stainless steel "L" shaped plate that is 5-10 mm long and 3-6 mm wide, with two stainless steel pins 2-5 mm in diameter. In one embodiment, an off axis wheel may engage the escapement mechanism with motor 104, and may comprise a 3-8 mm diameter 3-6 mm high cylinder with a hinge located asymmetrically 0.1-2 mm from the middle of the cylinder. The hinge may be a 2-5 mm diameter stainless steel pin.

The mechanical spring may be loaded using manual or automatic means via the loading port.

It may be noted that by preloading strut 100 with a sufficient store of energy for effectively treating a medical condition, actuator 104 may be precluded from exerting a force exceeding that which is required to controllably release preloader 102, thereby providing strut 100 with a relatively simple and/or small actuator 104.

Figure 1E:
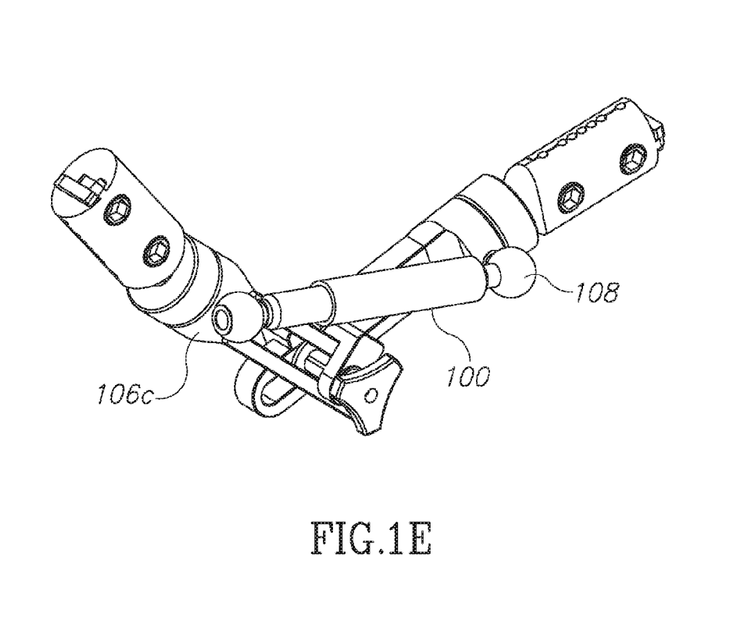
FIGS. 1E-F illustrate another perspective view of the strut of FIGS. 1A-D.
Figure 1F:
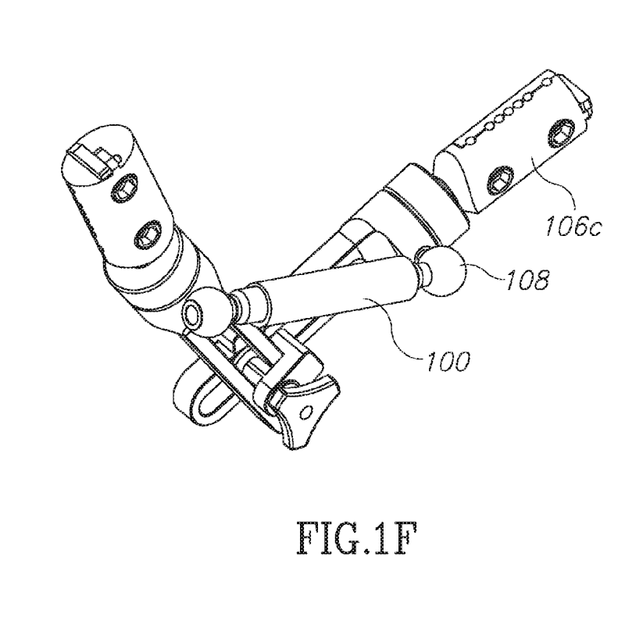

Reference is now made to FIG. 1E-F which illustrate strut 100 connected to a monorail fixator 106c. Strut 100 many operate as described above with respect to FIGS. 1A-D, responsive to one or more controlling signals from controller 122, such as in accordance with one or more signal received by sensor 126. Lengthening strut 100, as illustrated in FIG. 1E, may widen, or open monorail fixator 106c to exert a corresponding force on the bodily tissue, while shortening strut 100, such as illustrated in FIG. 1F, may narrow or close monorail fixator 106*c*. As with FIGS. 1C-D, for the purpose of clarity only, several features of FIGS. 1E-F are not labeled, however it is to be understood that any features described and/or labeled in FIGS. 1A-B similarly apply to FIGS. 1E-F.

Figure 2:
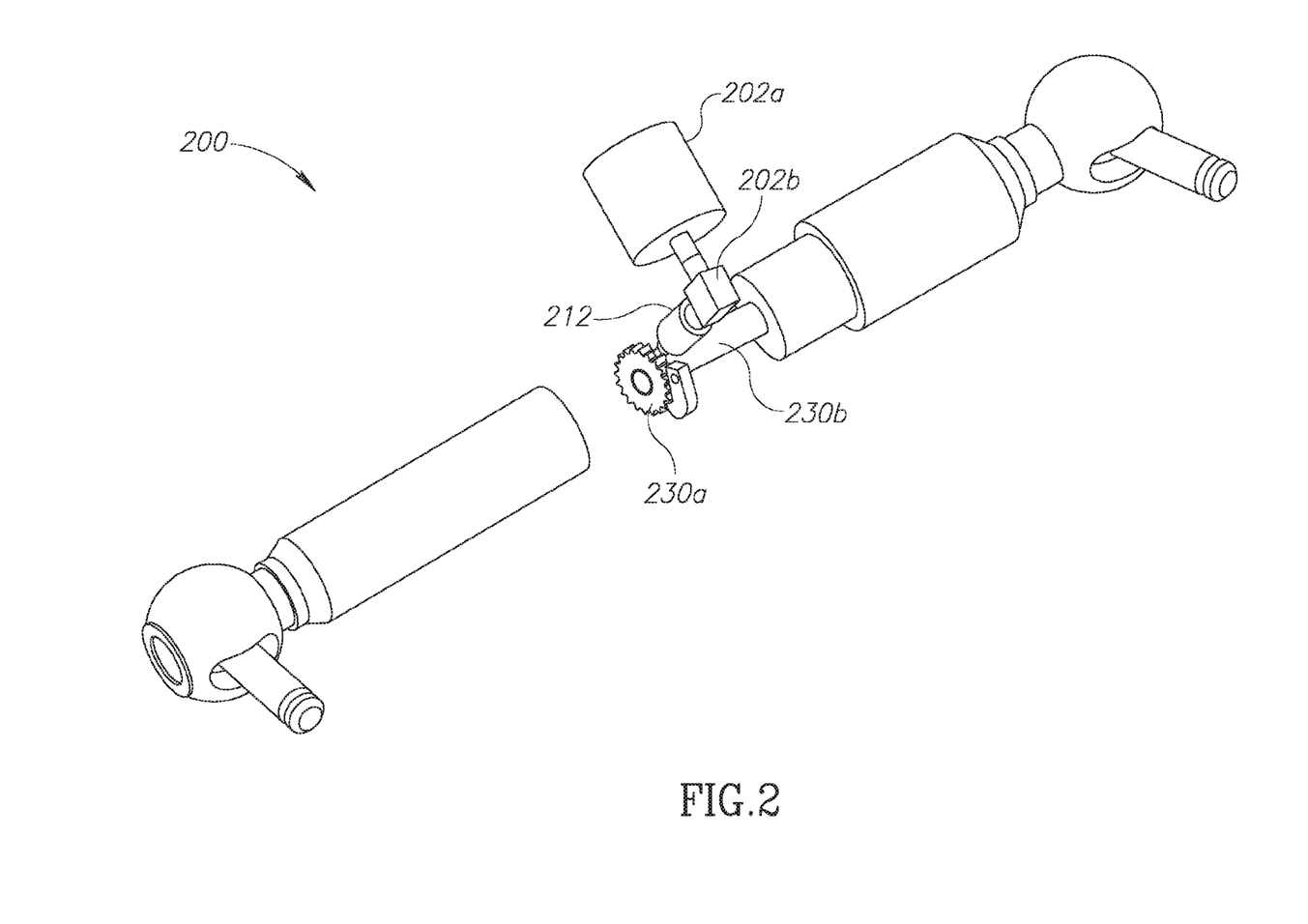
FIG. 2 illustrates an exploded view of a strut in accordance with another embodiment of the invention.

Reference is now made to FIG. 2 which illustrates a strut in accordance with another embodiment. A strut 200 may be disposed with a hydraulic mechanism for providing a force for adjusting the length of the strut. A hydraulic pump 202*b* may be provided for pumping a fluid from a reservoir 202*a* to exert a force on a piston 212. Piston 212 may engage with a gear 230*a* coupled to a treaded shaft, or bolt 230*b*. Thus, each pulse by piston 212 may cause a rotation of a predefined angle by the gear 230*a*, and which causes a corresponding rotation by the bolt 230*b*, resulting in an elongation of strut 200.

The force exerted by the hydraulic mechanism may be transferred by strut 200 to a bodily tissue, such as via an external fixation device connected to strut 200, as described above with respect to strut 100.

In one embodiment, gear 230*a* may have a diameter ranging from approximately 15 mm-30 mm, and bolt 230*b* may have a diameter ranging from approximately 3-10 mm. Gear 230*a* and bolt 230*b* may be made of any suitably rigid polymer, such as carbon fiber, stainless steel alloy or aluminum alloy.

In one embodiment, a ratchet mechanism, or latch (not shown) may be provided to prevent reverse rotation by gear 230*a*. The liquid reservoir 202*a* and pump 202*b* may be disposed within or external to strut 200. In one embodiment, the liquid reservoir 202*a* may be contained within the body of the fixation device, such as inside a hollowed out portion of the fixation device.

The liquid may be maintained in a closed system. After each pulse of piston 212, the liquid may be pumped back to the reservoir. In one embodiment, the reservoir may be made of an elastic material such as rubber or silicon that allows a volume decrease when liquid is pumped to piston 212 and a volume recovery at the end of each cycle of piston 212. The elastic material of the reservoir may contribute to the pressure drop at the direction that assists the pump to pump the liquid back to the reservoir.

In one embodiment, an anchor connector may be provided with strut 200. The anchor connector may comprise a pin approximately 8 mm to 15 mm long with a diameter typically between 2-4 mm and may be made of rigid polymer, carbon fiber, stainless steel or aluminum alloys.

In one embodiment, the elastic hydraulic liquid reservoir may be protected by a rigid chamber, such as may be made of a rigid polymer, carbon fiber, stainless steel alloy or aluminum alloy. The rigid chamber may be shape in accordance with any alignment requirement of one or more components of the external fixation devices.

In another embodiment, a micro hydraulic pump may be provided, such as a micro piezoelectric pump or a micro electric pump. The pump may operate in two directions, alternatively, the pump may comprise two pumps operating in opposite directions.

In an embodiment, the entrance diameter to piston 212 ranges from approximately 0.5 mm-3 mm, with a shaft diameter ranging from approximately 15 mm-30 mm. Piston 212 may be made of any suitable material, such as stainless steel alloy or aluminum alloy, and may have a linear configuration and align longitudinally with strut 200. Alternatively, piston 212 may have any other suitable shape, such as an L-shape.

Each pulse of the pump may cause an amount of liquid from reservoir to push piston 212 thereby causing the gear to rotate by a notch to lengthen strut 200. The ratchet mechanism may prevent the gear from turning in the reverse direction. After each cycle of piston 212, the pump may pump the liquid back to the reservoir, causing piston 212 to retract until the next pulse by the pump.

As described above with respect to FIGS. 1A-D, strut 200 may be provided with one or more controllers 222 (not shown) that control any of the components of strut 200, and/or the hydraulic mechanism comprising the pump driving piston 212. Controller 222 may receive one or more indicators measured by a sensor 226 (not shown), such as may be similar to sensor 126 described above, and may analyze the indicator to monitor, control and/or synchronize the operation of any components of strut 200, accordingly. Controller 222 may communicate with an external controlling device 224 as described, and receive from device 224 a parameter for controlling any of the components of strut 200. Controller 222 may send the indicator measured by sensor 226 to an operator, such as physician, via device 224, and may receive the parameter in response to device 224 receiving the indicator.

The present invention may be a system, a method, and/or a computer program product. The computer program product may include a computer readable storage medium (or media) having computer readable program instructions thereon for causing a processor to carry out aspects of the present invention.

The computer readable storage medium can be a non-transitory, tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention may be described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Numerous modifications and alternative embodiments of the present invention will be apparent to those skilled in the art in view of the foregoing description. Accordingly, this description is to be construed as illustrative only and is for the purpose of teaching those skilled in the art the best mode for carrying out the present invention. Details of the structure may vary substantially without departing from the spirit of the present invention, and exclusive use of all modifications that come within the scope of the appended claims is reserved. Within this specification embodiments have been described in a way which enables a clear and concise specification to be written, but it is intended and will be appreciated that embodiments may be variously combined or separated without parting from the invention. It is intended that the present invention be limited only to the extent required by the appended claims and the applicable rules of law.

It is to be understood that the following claims are to cover all generic and specific features of the invention described herein, and all statements of the scope of the invention which, as a matter of language, might be said to fall therebetween.

What is claimed is:

1. A medical device, comprising:
    a medical strut shaped and sized to be connected to one or more external fixation devices positioned outside a body;
    a preloader configured to store energy, wherein the medical strut is configured to transform the energy stored in the preloader to a first force applicable to a bodily tissue;
    an actuator configured to apply a second force on said preloader to facilitate the transforming of said stored energy to said first force, thereby adjusting the length of the medical strut; and
    a controller configured to control the actuator;
    wherein the actuator is further configured to shorten the medical strut independently of the preloader.

2. The medical device of claim 1, wherein the actuator comprises a motor, and wherein the second force comprises a torque.

3. The medical device of claim 1, wherein the adjusting of the length of the medical strut comprises lengthening the medical strut.

4. The medical device of claim 1, wherein the first force is exerted longitudinally along the lengthwise axis of the medical strut.

5. The medical device of claim 1, wherein said one or more external fixation devices are connectable to the bodily tissue via one or more pins, thereby transferring the first force to the bodily tissue.

6. The medical device of claim 5, wherein the medical strut connects to the one or more external fixation devices via a mechanism that provides polyaxial movement of the medical strut with respect to the one or more external fixation devices.

7. The medical device of claim 5, wherein said one or more external fixation devices comprises a monorail fixator.

8. The medical device of claim 1, wherein the preloader comprises a spring.

9. The medical device of claim 8, wherein the spring comprises a sealed cavity that is configured to store a fluid under high pressure.

10. The medical device of claim 1, wherein the controller controls any of: a duration for operating the actuator, a force exerted by the actuator, or a target medical strut length.

11. The medical device of claim 1, wherein the controller controls a target bone lengthening rate.

12. The medical device of claim 1, wherein said actuator is configured to lengthen said medical strut predominantly by applying said second force on said preloader mostly to facilitate the transforming of said stored energy to said first force.

13. The medical device of claim 1, wherein said preloader is loaded with energy prior to connection to said medical strut.

14. The medical device of claim 1, wherein said actuator is integral to said medical strut.

15. A kit for providing a medical treatment, comprising:
a medical strut shaped and sized to be positioned outside a body comprising:
a preloader configured to store energy, wherein the medical strut is configured to transform the energy stored in the preloader to a first force applicable to a bodily tissue,
an actuator configured to apply a controlled second force on said preloader to facilitate the transforming of said stored energy to said first force, thereby adjusting the length of the medical strut, and
a controller that is configured to control the actuator; and
an external fixation device configured to connect to the medical strut and to connect to the bodily tissue via one or more pins, thereby transferring the first force to the bodily tissue;
wherein said actuator is further configured to shorten the medical strut independently of the preloader.

16. The kit of claim 15, wherein the actuator comprises a motor, and wherein the second force comprises a torque.

17. The kit of claim 15, wherein the adjusting of the length of the medical strut comprises lengthening the medical strut.

18. The kit of claim 15, wherein the medical strut connects to the external fixation device via a mechanism that provides polyaxial movement of the medical strut with respect to the external fixation device.

19. The kit of claim 15, wherein the preloader comprises a spring.

20. The kit of claim 19, wherein the spring comprises a sealed cavity that is configured to store a fluid under high pressure.

21. The kit of claim 15, wherein the controller controls any of: a duration for operating the actuator, a force exerted by the actuator, or a target medical strut length.

22. The kit of claim 15, wherein said actuator is configured to lengthen said medical strut predominantly by applying said second force on said preloader to facilitate the transforming of said stored energy to said first force.

23. The kit of claim 15, wherein said preloader is loaded with energy prior to connection to said medical strut.

24. The kit of claim 15, wherein said actuator is integral to said medical strut.

25. A method comprising:
transforming, via a medical strut, energy stored by a preloader to a first force for applying to a bodily tissue;
applying, via an actuator, a second force on said preloader to facilitate the transforming of said stored energy to said first force, thereby adjusting the length of the medical strut; and
controlling the actuator;
shortening the medical strut by said actuator independently of the preloader.

26. The method of claim 25, further comprising connecting the medical strut to one or more external fixation devices that are connected to the bodily tissue via one or more pins, thereby transferring the first force to the bodily tissue.

27. The method of claim 26, further comprising providing polyaxial movement of the medical strut with respect to the one or more external fixation devices.

28. The method of claim 26, wherein said one or more external fixation devices comprise a monorail fixator.

29. The method of claim 25, wherein said adjusting the length of said medical strut comprises lengthening the medical strut predominantly by transforming said energy stored in said preloader to said first force.

* * * * *